United States Patent [19] [11] 4,202,103
Zall et al. [45] May 13, 1980

[54] MATRIX BAND GUIDE AND MATRIX RETAINER DEVICE

[76] Inventors: Michael E. Zall, Two Yorkshire Dr., Suffern, N.Y. 10901; Stephen Silverhardt, 1436 Marshall La., Meadowbrook, Pa. 19046

[21] Appl. No.: 771,616

[22] Filed: Feb. 24, 1977

[51] Int. Cl.² .............................................. A61C 5/12
[52] U.S. Cl. .................................... 433/153; 433/154
[58] Field of Search ............................................ 32/63

[56] References Cited

U.S. PATENT DOCUMENTS

| | | | |
|---|---|---|---|
| 531,833 | 1/1895 | Bruce | 32/63 |
| 911,307 | 2/1909 | Ivory | 32/63 |
| 2,500,867 | 3/1950 | Reiter | 32/63 |
| 2,502,903 | 4/1950 | Tofflemire | 32/63 |
| 2,560,553 | 7/1951 | Christie et al. | 32/63 |
| 4,024,643 | 5/1977 | Eisenberg | 32/63 |

*Primary Examiner*—Louis G. Mancene
*Assistant Examiner*—John J. Wilson
*Attorney, Agent, or Firm*—Michael E. Zall

[57] ABSTRACT

A matrix band guide for use in simultaneously applying a matrix band to a plurality of teeth. The guide is a flexible elongated member having a plurality of slots. The elongated member is of sufficient length and of sufficient width to allow placement of the guide against the teeth and to guide the matrix band around the teeth. The slots are of a width, height and spacing sufficient to permit the looping of the matrix band through the slots to form a plurality of loops for binding engagement with the teeth. When the matrix band is drawn into binding engagement with the teeth, the elongated member and the matrix band substantially conform to the taper and curvature of the teeth.

The guide, may have a mounting means for mounting the elongated member to a conventional matrix retainer in such a manner that the matrix band can be drawn into binding engagement with the teeth by the conventional matrix retainer.

The elongated member may also be shaped to substantially conform to the alignment of the teeth.

A matrix retainer device for use in simultaneously applying a matrix band to a plurality of teeth. The matrix retainer device is, broadly, the aforementioned matrix band guide in combination with a means for drawing the matrix band into binding engagement with the teeth.

29 Claims, 7 Drawing Figures

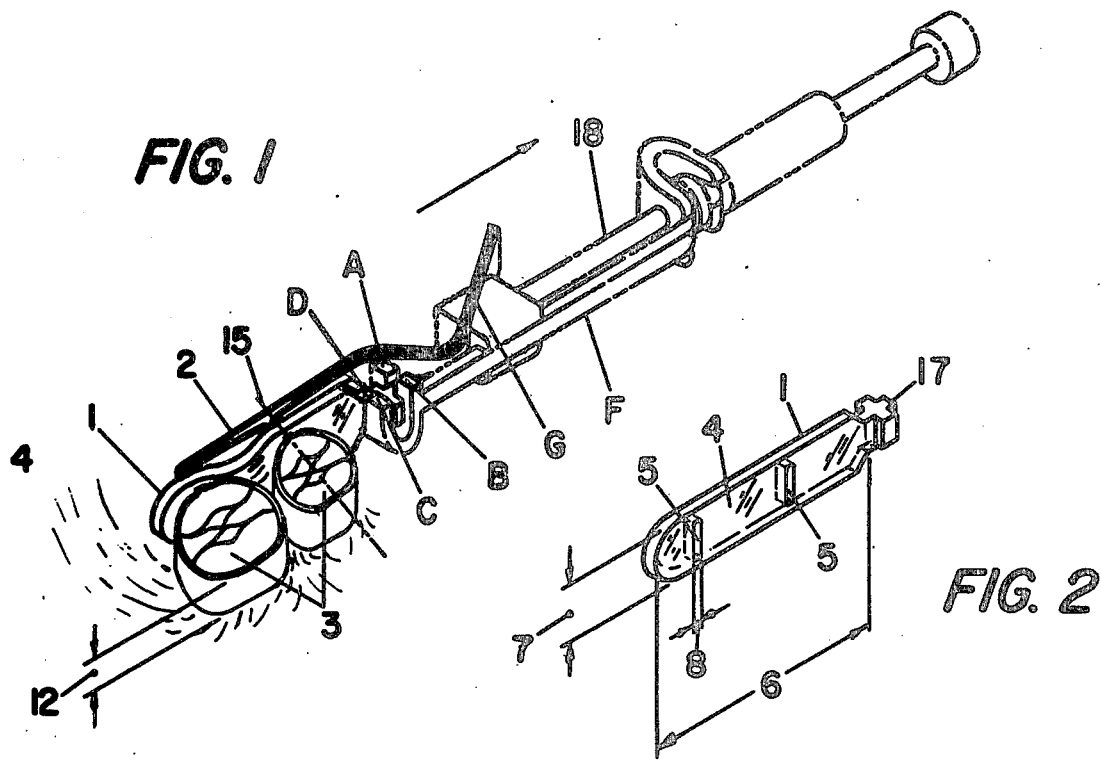
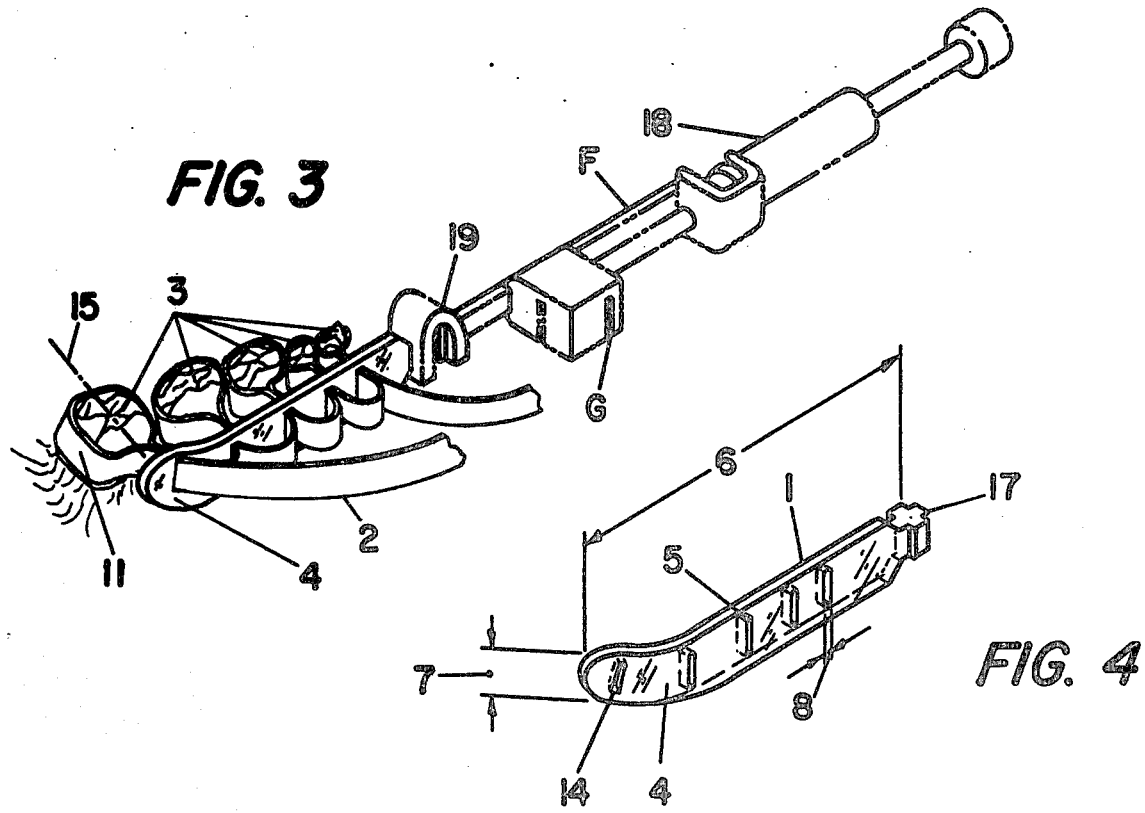

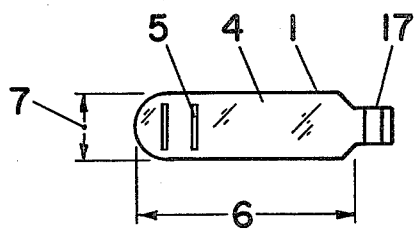
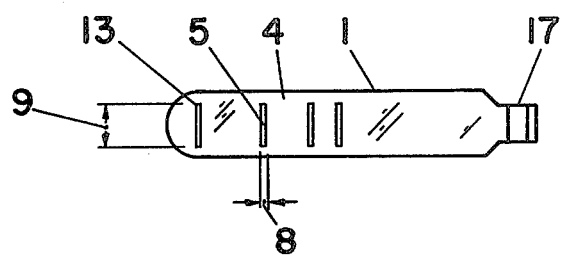
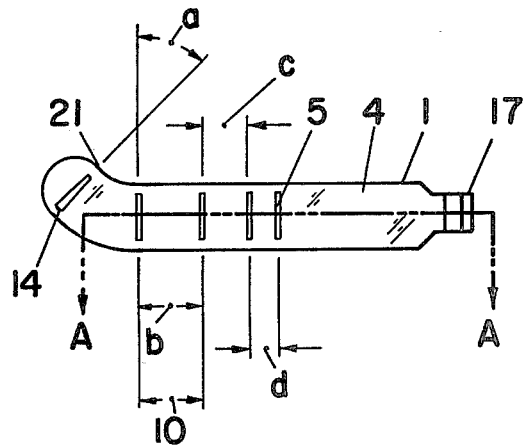
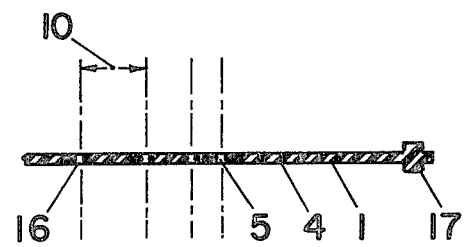
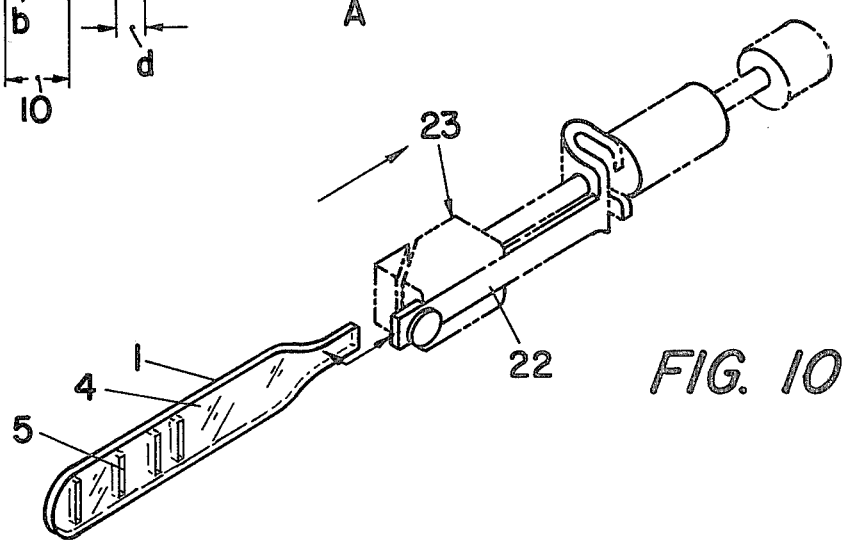

MATRIX BAND GUIDE AND MATRIX RETAINER DEVICE

The present invention relates to a matrix band guide and a matrix retainer device of the type utilized in a procedure wherein a matrix band is applied to a tooth or a plurality of teeth and drawn into binding engagement with the tooth or plurality of teeth.

Generally, matrix bands are thin, highly flexible metal bands (usually made of stainless steel) which prior to filling a cavity are applied to a tooth and drawn into binding engagement with the tooth so that the matrix band substantially conforms to the taper and curvature of the tooth. This procedure is performed to enable the dentist to fill the cavity so that the filling material i.e., amalgam, will not project beyond the surfaces of the tooth. If the filling material projects beyond the surfaces of the tooth, food particles may be retained producing an area for potential development of cavities.

Due to the taper and curvature of a normal tooth it is impossible for a matrix band to conform closely enough to the contour of the tooth without a means for drawing the matrix band into binding engagement with the tooth. Consequently, various devices and arrangements have been developed in attempts to accomplish this drawing of the matrix band. Some of these devices, i.e., the "Tofflemire" and "Ivory" matrix retainer devices, have met with widespread acceptance and use by the dental profession.

One major defect with most of the known matrix retainer devices is that they are only capable of drawing a matrix band into binding engagement with only one tooth. Generally, no provision is made for simultaneously applying a matrix band to a plurality of teeth.

Since cavities often occur in adjacent teeth, it is often highly desirable that a plurality of adjacent teeth be filled simultaneously.

It is also highly desirable for the efficient utilization of time by the dentist to fill, simultaneously, a plurality of teeth which are not necessarily adjacent to each other, but are in the same quadrant of the mouth.

Further, with the advent of third party payments to dentists (Blue Cross, Blue Shield, Medicaid, Medicare, etc.), socialized systems of medicine in some countries, and lower fee schedules demanded by patients and governmental agencies, dental professionals are continuously attempting to utilize their time more efficiently and perform dental procedures more rapidly.

As previously stated most of the known matrix retainer devices are incapable of simultaneously applying a matrix band to a plurality of teeth. Known devices which have been designed to simultaneously apply a matrix band to a plurality of teeth have not met with acceptance by the dental profession due to the complexity in design and use and the concommitant increase in the cost of such devices. Further, some of these known devices are limited in their use in that they can only be utilized, at best, on only two teeth.

Typical prior art matrix retainer devices which only apply a matrix band to a single tooth are described in the following U.S. Pat. Nos.: 887,478; 2,791,030; 911,307; 2,811,777; 943,353; 2,964,847; 980,529; 2,995,822; 2,374,750; 3,020,638; 2,439,703; 3,046,659; 2,502,903; 3,105,301; 2,538,486; 3,105,402; 2,588,059; 3,145,472; 2,591,745; 3,305,928; 2,594,367; 3,237,307; 2,611,182; 3,377,705; 2,714,252; 3,436,831; and 2,720,701; 3,517,444.

The entire disclosures of all of the aforementioned U.S. Patents are herein incorporated by reference.

The aforementioned patents described what is termed herein "the conventional matrix retainer". The conventional matrix retainer can generally be described as a device having a means for guiding a matrix band around a single tooth and a means for drawing the band into binding engagement with the tooth. An example of a conventional matrix retainer which has found widespread acceptance and use by the dental profession is described in U.S. Pat. No. 2,502,903.

The conventional matrix retainer devices are generally known in the dental profession as "Tofflemire" or "Ivory" matrix retainers. It should be noted that these names for the matrix retainers are derived from the patentees of said devices. All of the aforementioned U.S. Patents have "Tofflemire" or "Ivory" as patentees.

Several known devices have attempted to apply a matrix band to a plurality of teeth. Typical of these prior art devices are U.S. Pat. Nos. 2,560,553, 2,636,269 and 2,286,021.

U.S. Pat. No. 2,560,553 describes a complicated device having, inter alia, rotating ribbon guides. The device is very complicated, cumbersome to utilize and costly. It has not found widespread acceptance by the dental profession. This is the only known device, to applicant's knowledge, which has attempted to apply a matrix band to more than two teeth. U.S. Pat. No. 2,636,269 and 2,286,021 describe the application of a matrix band to only two adjacent teeth.

An object of the present invention is to provide a matrix band guide and a matrix retainer device which applies a matrix band to a plurality of teeth.

A further object of this invention is to provide a matrix band guide and matrix retainer device wherein provision is made for simultaneously applying a matrix band to a plurality of adjacent teeth, and wherein the cavities in said teeth are filled simultaneously.

A still further object of this invention is to provide a matrix band guide and a matrix retainer device wherein provision is made for simultaneously applying a matrix band to a plurality of teeth, not necessarily adjacent to each other, but in the same quadrant of the mouth, wherein the cavities in said teeth are filled simultaneously.

A further object of this invention is to provide a matrix band guide and matrix retainer device for a plurality of teeth in which the matrix band is maintained in uniform tension, i.e. binding engagement, about all of the teeth surrounded by the matrix band.

A further object of this invention is to provide a matrix band guide which is simple to construct, inexpensive and can be utilized with conventional matrix retainer devices.

A further object of this invention is to provide a matrix band guide which can be detachably mounted to conventional matrix retainer devices in such a manner that the matrix band can be drawn into binding engagement with the teeth by the conventional matrix retainer device.

A further object of this invention is to provide a matrix band guide which can be detachably mounted to conventional matrix retainer devices and which may be disposed of after use.

Other objects of this invention will be apparent from the accompanying specification, claims and drawings.

DRAWINGS

FIG. 1 is a perspective view of a preferred embodiment of the matrix band guide attached to a conventional matrix retainer device and in use;

FIG. 2 is a perspective view of the matrix band guide of FIG. 1 detached from the conventional matrix retainer device;

FIG. 3 is a perspective view of another preferred embodiment of the matrix band guide attached to the conventional matrix retainer device and being prepared for use;

FIG. 4 is a perspective view of the matrix band guide of FIG. 3, detached from the conventional matrix retainer device;

FIG. 5 is a side elevation of a preferred embodiment of the matrix band guide for use on up to two teeth;

FIG. 6 is a side elevation of still another preferred embodiment of the matrix band guide for use on up to three teeth;

FIG. 7 is a side elevation of still another preferred embodiment of the matrix band guide for use on up to four teeth;

FIG. 8 is a side elevation of still another preferred embodiment of the matrix band guide for use on up to five teeth;

FIG. 9 is a view of A—A of FIG. 8; and

FIG. 10 is a perspective view of a preferred embodiment of the matrix retainer device of this invention.

DETAILED DESCRIPTION OF THE INVENTION

Referring now to the drawings, in detail, the matrix band guide is designated generally as (1). The matrix band guide (1) is used for simultaneously applying a matrix band (2) to a plurality of teeth (3). The guide (1) is a flexible elongated member (4) having a plurality of slots (5). The elongated member (4) is of sufficient length (6) and of sufficient width (7) to allow placement of the guide (1) against the teeth (3) and to guide the matrix band (2) around the teeth (3). The slots (5) are of a width (8), height (9) and spacing (10) sufficient to permit the looping of the matrix band (2) through the slots (5) to form a plurality of loops (11) for binding engagement with the teeth (3). When the matrix band (2) is drawn into binding engagement with the teeth (3), the elongated member (4) and the matrix band (2) substantially conform to the taper and curvature of the teeth (3).

Generally, the matrix band (2) utilized in this invention is constructed of thin, flexible stainless steel. Matrix bands (2) currently used in the dental profession are suitable for use with this invention. The matrix band (2) should be of a length sufficient for use in forming the plurality of loops (11) which are placed around the teeth (3) and for drawing into binding engagement with the teeth (3). Typically, the matrix bands (2) are of a width (12) of from about ¼" to about ½". The width (12) of the matrix band (2) is sufficient to wrap the height of the tooth completely in the matrix band (2). The matrix band (2) is thin enough to fit between the teeth (3). The matrix bands (2) utilized with this invention are well known in the art and readily available to the dental profession.

The matrix band (2) is applied to a plurality of teeth (3). Generally this invention envisions applying the matrix band (2) to any number of teeth. Preferably, however the teeth should be in the same quadrant of the mouth. This invention is particularly advantageous when filling adjacent teeth, however this invention may also be utilized in filling a plurality of teeth which are not necessarily adjacent to each other, but are in the same quadrant. This invention is particularly advantageous in filling the upper and lower molar and premolar teeth. Generally, however, this invention may be utilized wherein a plurality of teeth (3) require the simultaneous application of a matrix band (2) around them.

The flexible elongated member (4) may be constructed of any material flexible enough so that when the matrix band (2) is drawn into binding engagement with the teeth (3) the elongated member (4) and the matrix band (2) substantially conform to the taper and curvature of the teeth (3). Preferably, the flexible elongated member (4) is constructed of a polymeric material, for example polyethylene. More preferably, however, the flexible elongated member (4) is transparent to allow the dentist utilizing the matrix band guide (1) to observe the placement of the matrix band (2) around the teeth (3). This invention, however, envisions the flexible elongated member being constructed of any type material having sufficient flexibility to perform its intended function.

The flexible elongated member (4) is of sufficient length (6) and sufficient width (7) to allow placement of the guide (1) against the teeth (3) and to guide the matrix band (2) around the teeth (3). Generally, the length (6) of the elongated member (4) is dictated by the number of teeth (3) for which the matrix band guide (1) is designed. Preferably the matrix band guide (1) should be designed for use on from two to five teeth. Generally, it has been found that when using a matrix band guide (1) for five teeth the length (6) of the elongated member (4) should generally be about three inches. This length allows the matrix band (2) to be placed around all five teeth (3) and is of sufficient length (6) to allow the dentist to manipulate the matrix band guide (1) in the mouth. Obviously, the flexible elongated member may be shorter when it is being utilized for four or less teeth.

The width (7) of the elongated member is generally at least the height of the teeth for which the matrix band guide (1) is being utilized. In the preferred embodiment of this invention, the width (7) is generally somewhat wider than the width (12) of the matrix band (2), although this invention envisions a flexible elongated member (4) which may be of a width (7) less than the width (12) of the matrix band and which has slots (5) which are not closed at the top (13). However, it has been found that this embodiment of the invention is cumbersome in "loading", i.e. placing the matrix band (2) in the guide (1) and around the teeth (3).

For general guidance it has been found that a matrix band guide (1) of a width (7) of about ½ inch is suitable.

The slots (5) are generally of a width (8), height (9) and spacing (10) sufficient to permit the looping of the matrix band (2) through the slots (5) to form a plurality of loops (11) for binding engagement with the teeth. Generally, the slots (5) should be of a height (9) somewhat greater than the matrix band width (12). It has been found that a matrix band ¼ inch in width is preferred. Thus, a preferred height (9) of the slot is about 5/16 of an inch. As indicated previously, this invention envisions a slot which is not necessarily closed at the top (13) and thus the height of the slot may be substantially less than the matrix band. However, such a device, although envisioned by this invention and operable, is somewhat cumbersome to utilize.

The width (8) of the slot is of a width greater than twice the thickness of the matrix band. Generally, it has been found that a 1/32 inch width (8) is sufficient. However, this invention envisions any slot width (8) as long as the matrix band (2) can be drawn into binding engagement with the teeth (3) and the matrix band (2) performs its intended function of enabling the dentist to fill the cavity so that filling material, i.e. amalgam, will not project beyond the surfaces of the teeth.

It has been found that when the elongated member (4) is shaped to substantially conform to the alignment of the teeth in the jaw it is desirable to have the slots (5) shaped in such a manner so that when the matrix band (2) is drawn into binding engagement with the teeth the band can be drawn easily through the slots. This might require a triangular configuration (14) to the last slot on the elongated member (4).

The spacing of the slots (10) should be sufficient to permit the plurality of loops (11) formed from the matrix band (2) to be wrapped around the plurality of teeth (3). Proper dental practice indicates that when the matrix band (2) is drawn into binding engagement with the teeth (3) and the elongated member (4) and the matrix band substantially conform to the taper and curvature of the teeth, the slots (5) should be about at the center (15) of the teeth (3) being filled (FIG. 1). Generally, referring to FIGS. 8 and 9, it has been found in the preferred embodiment of this invention (which is designed to apply a matrix band to the three molar teeth and two pre-molar teeth) that spacing (a) should be about ⅜ of an inch, spacing (b) should be about 7/16 of an inch spacing (c) should be about 5/16 of an inch and spacing (d) should be about 3/16 of an inch. The spacing between the slots should be such that one matrix band guide design may be utilized for many patients. However, this invention envisions having a matrix band guide designed for a particular type of patient, i.e. child, teenager, adult. Such a matrix band guide design would require different spacing between the slots for each particular type of person.

The slot edges are preferrably shaped or treated to facilitate the drawing of the matrix band into binding engagement with the teeth. For example, as shown in FIG. 9, edges (16) may be tapered, rounded or even lubricated to facilitate easy drawing of the matrix band.

The matrix band (2) is passed through the slots (5) to form a plurality of loops (11). The matrix band loops (11) are guided around the teeth (3) by the matrix band guide (1). In use, the matrix band (2) is drawn into binding engagement with the teeth. The elongated member (4) and the matrix band (2) are drawn in such a manner that the elongated member (4) and the matrix band (2) substantially conform to the taper and curvature of the teeth (3). After the matrix band is drawn tightly around the teeth, the cavities of the teeth are filled.

The matrix band guide (1) is preferably further comprised of a mounting means (17) for mounting the elongated member (4) to a conventional matrix retainer (18). The elongated member (4) is mounted to the conventional matrix retainer (18) in such a manner that the matrix band (2) can be drawn into binding engagement with the teeth (3) by the conventional matrix retainer (18). Preferably this mountng means is a detachable mounting means for detachably mounting the elongated member (4) to the conventional matrix retainer (18).

Generally, this invention contemplates any type mounting means and any type conventional matrix retainer.

As previously indicated the conventional matrix retainer device (18) is generally comprised of a matrix band guide (19) for applying a matrix band to a single tooth and a means for drawing the matrix band into binding engagement with the tooth.

A typical conventional matrix retainer device (18) which has found widespread acceptance and use by the dental profession is exemplified by U.S. Pat. No. 2,502,903, the entire disclosure of which is herein incorporated by reference.

This conventional matrix retainer device (18) is illustrated in FIGS. 1 and 3, in use in conjunction with the matrix band guide (1) of this invention.

Generally, as indicated previously, the mounting means (17) for mounting the elongated member (4) to such a conventional matrix retainer (18) can be any type mounting means which mounts the elongated member (4) in such a manner that the matrix band can be drawn into binding engagement with the teeth by the conventional matrix retainer.

For example, as depicted in FIGS. 1 and 3, the elongated member can be frictionally attached to the four parallel and spaced apart fingers A, B, C and D. This frictional mount is a detachable mounting means, in that one can attach and detach the elongated member (4). Further, if the elongated member (4) is shaped to substantially conform to the alignment of the teeth it may be necessary to detach the elongated member (4) and turn it over for use on the other side of the mouth.

The mounting means (17) for mounting the elongated member (4) to such a conventional matrix retainer device (18) should align the elongated member (4) in such a manner that a movement of the sliding block along the bar (F) will move the matrix band ends therewith in such a manner that the matrix band loops (11) are drawn into binding engagement with the teeth (3). Generally, the slots (5) in the elongated member (4) should be in substantial alignment with the slots defined by the fingers A, B, C and D. Thus, when the matrix band (2) is drawn into binding engagement, the matrix band (2) will be drawn smoothly and frictional binding between the matrix band, the elongated member, and the conventional matrix retainer device will be minimized.

Preferably the elongated member (4) is shaped to substantially conform to the alignment of the teeth. Generally, this will result in a curvature (21) (See FIG. 8) of the elongated member (4) to accomodate the third molar tooth. When such a curvature (21) is present the elongated member (4) may be utilized on either side of the mouth by merely detaching the matrix band guide (1) from the conventional matrix retainer device (18), turning it over and attaching the matrix band guide (1) to the conventional matrix retainer device (18). Thus, the matrix band guide (1) when such curvature (21) is present may be utilized for the right and the left sides of the mouth.

When, however, a matrix band guide does not have to accomodate the third molar, the elongated member (4) may be substantially straight. The flexibility of the elongated member will allow the elongated member to substantially conform to the alignment of the teeth. This invention, however, envisions at one extreme a perfectly straight elongated member and at the other extreme an elongated member which has been substantially molded to conform to the alignment, curvature and taper of the teeth, i.e. a custom fitted elongated member. An essential element of this invention is that when the matrix band (2) is drawn into binding engagement with the teeth (3) the elongated member (4) and the matrix band (2) substantially conform to the taper and curvature of the teeth (3). As stated previously this may be accomplished by shaping the elongated member and/or providing a certain flexibility to the elongated member.

The invention envisions a matrix band guide (1) having any number of slots such that the matrix band guide may be used for simultaneously applying a matrix band to a plurality of teeth. Preferably, the elongated member should have no more than five slots so that a matrix band may be simultaneously applied to the first and second premolars and the first, second and third molar teeth. As previously indicated, when the matrix band guide is designed to accomodate all of these five teeth the elongated member should be shaped (21) to substantially conform to the alignment of the teeth.

This invention however envisions matrix band guides having two, three and four slots to accomodate respectively, two, three and four teeth at a time (FIGS. 5 through 9). When utilizing the matrix band guide it is not necessary that all of the slots be utilized to apply the matrix band to the teeth. For example, the teeth do not necessarily have to be adjacent to each other to utilize the matrix band guide. The matrix band guide may apply a matrix band to the first pre-molar and the first molar tooth skipping the application of the matrix band to the second pre-molar tooth.

Thus, if cavities have not developed in adjacent teeth, but have developed in a quadrant of the mouth the matrix band guide may be utilized to apply the matrix band to the teeth having the cavities in them.

As depicted in all of the Figures attached hereto, the slots (5) in the elongated member (4) are closed at both ends (13). This invention, however, envisions the use of slots which may be opened at one end. It has been found, however, when utilizing such a device that the matrix band guide and the matrix band become extremely cumbersome to manipulate and to place on the plurality of teeth. However, for example, when there are only two slots in the elongated member, such type slot may be practical. As indicated however, it is preferred that all of the slots be closed at both ends.

This invention further visualizes a matrix retainer device (22) for use in simultaneously applying a matrix band to a plurality of teeth (FIG. 10). The matrix retainer device is comprised of a flexible elongated member (4) having a plurality of slots (5). The elongated member (4) is sufficient length and sufficient width to allow placement of the guide against the teeth and to guide the matrix band around the teeth. The slots are of a width, height and spacing sufficient to permit the looping of the matrix band through the slots to form a plurality of loops for binding engagement with the teeth. The matrix retainer device is further comprised of a means for drawing (23) the matrix band into binding engagement with the teeth. Such a means for drawing the matrix band into binding engagement with the teeth is envisioned in FIG. 10. In effect the means for drawing the matrix band into binding engagement with the teeth is well known in the art and is basically that part of the conventional matrix retainer device (18).

When the matrix band is drawn into binding engagement with the teeth the elongated member and the matrix band substantially conform to the taper and curvature of the teeth.

All of the numerous variations on the elongated member described previously may be incorporated in the matrix retainer device. In effect, the matrix retainer is substantially the matrix band guide attached to a means for drawing the matrix band into binding engagement with the teeth. The elongated member (4) may be either permanently attached to the means for drawing or may be detachably mounted to the means for drawing to allow removal of the elongated member and replacement with another type elongated member.

It has also been found that it is desirable that the elongated member be transparent. This allows the dentist to see exactly how the matrix band is being placed around the plurality of teeth and to see how the filling of the cavity is proceeding. Various polymeric materials can provide this transparency to the elongated member.

This invention envisions a matrix band guide which may be disposable, semi-disposable or of a more permanent nature. By the term "disposable" it is meant that after each use of the matrix band guide it is disposed of. By the term "semi-disposable" it is meant that after several, i.e. two, three, four or more, uses of the matrix band guide, is disposed of. By the use of the term "permanent" it is meant that the matrix band guide may be utilized numerous times without deterioration of the guide. Both the semi-disposable and and permanent type matrix band guides, should be made of a material which will allow for "cold sterilization", a procedure well known to the dental profession. The "disposable" type matrix band guides should be manufactured, packaged and sold under sterile conditions for immediate utilization by the dentist.

This invention further envisions the possibility of matrix band guides coming in "sets", that is a number of matrix band guides adapted for a number of dental situations. For example, a patient may come in with the first pre-molar and first molar teeth needing filling. The matrix band guide used might be designed with slots spaced in such a manner to accommodate the simultaneous application of the matrix band to the first pre-molar and the first molar teeth. There may be a matrix band guide to accomodate two, three, four or five teeth at a time in varying positions in the mouth.

Referring now to FIGS. 1 and 3, the operation of the matrix band guide will be described in connection with the filling of a plurality of teeth. The possiblity of using the matrix band guide and matrix retainer device with adjacent teeth is of considerable importance as previously explained, in that cavities commonly occur in adjacent teeth. As will be apparent from the drawing, the matrix band is threaded through the slots to form a plurality of loops. The matrix band is brought back to the matrix clamping block where the two ends are threaded through the diagonally extending slots (G) to receive the end sections of the matrix band (2). The loops of the matrix band are then placed over the teeth containing the cavities to be filled, and while the loops of the matrix band are retained in place the block is moved along the bar (F) to draw the matrix band into binding engagement with the teeth. The flexible elongated member (4) and the matrix band (2) are made to substantially conform to the taper and curvature of the teeth by the tension produced on the matrix band. If it is found that the friction between the teeth (3) and the matrix band (4) is greater than desired a lubricating ointment may be placed upon the teeth. However, it has been found that the moisture of the mouth or water placed upon the teeth is sufficient to allow the proper drawing of the matrix band.

The matrix band loops may be readily removed from the teeth by loosening the matrix band and slipping the loops off the teeth. It may be desirable, however, to cut the matrix band so that the filling material will not be disturbed by the slipping off the loops off the teeth.

It will be seen that we have provided a matrix band guide and a matrix retainer device in which it is possible to simultaneously apply a matrix band to a plurality of teeth. It will also be apparent that the matrix band guide and the matrix retainer device are extremely simple in character and can be readily manufactured and utilized.

Although in practice it has been found that the form of the invention illustrated herein and referred to in the above description as the preferred embodiments is the most efficient and practical, yet realizing the conditions concurrent with the adoption of this invention will necessarily vary, it is desired to emphasize that various minor changes in details of construction, proportion and arrangement of parts, may be resorted to within the scope of the appended claims without departing from or sacrificing any of the principals of this invention.

We claim:

1. A matrix band guide for use in simultaneously applying a matrix band to a plurality of teeth comprised of a flexible elongated member having a plurality of slots, wherein the elongated member is of sufficient length and sufficient width to allow placement of the guide against the teeth and to guide the matrix band around the teeth, and wherein the slots extend a major portion of the width of the member and are of a width, height and spacing sufficient to permit the looping of the matrix band through the slots to form a plurality of loops for binding engagement with the teeth, whereby when the matrix band is drawn into binding engagement with the teeth the elongated member and the matrix band substantially conform to the taper and curvature of the teeth.

2. The matrix band guide of claim 1, wherein the elongated member is shaped to substantially conform to the alignment of the teeth.

3. The matrix band guide of claim 1, wherein there are five slots.

4. The matrix band guide of claim 1, wherein there are four slots.

5. The matrix band guide of claim 1, wherein there are three slots.

6. The matrix band guide of claim 1, wherein there are two slots.

7. The matrix band guide of claim 1, wherein the slots are closed at both ends.

8. The matrix band guide of claim 1, wherein the elongated member is transparent.

9. A matrix band guide for use in simultaneously applying a matrix band to a plurality of teeth comprised of:

a flexible elongated member having a plurality of slots, wherein the elongated member is of sufficient length and sufficient width to allow placement of the guide against the teeth and to guide the matrix band around the teeth, and wherein the slots extend a major portion of the width of the member and are of a width, height and spacing sufficient to permit the looping of the matrix band through the slots to form a plurality of loops for binding engagement with the teeth; and a mounting means for mounting the elongated member to conventional matrix retainer in such a manner that the matrix band can be drawn into binding engagement with the teeth by the conventional matrix retainer, whereby when the matrix band is drawn into binding engagement with the teeth, the elongated member and the matrix band substantially conform to the taper and curvature of the teeth.

10. The matrix band guide of claim 9, wherein the mounting means is a detachable mounting means for detachably mounting the elongated member to the conventional matrix retainer.

11. The matrix band guide of claim 9, wherein there are five slots.

12. The matrix band guide of claim 9, wherein the slots are closed at both ends.

13. The matrix band guide of claim 9, wherein the elongated member is transparent.

14. The matrix band guide for use in simultaneously applying a matrix band to a plurality of teeth comprised of:

a flexible elongated member having a plurality of slots, wherein the elongated member is of sufficient length and sufficient width to allow placement of the guide against the teeth and to guide the matrix band around the teeth, is shaped to substantially conform to the alignment of the teeth and wherein the slots extend a major portion of the width of the member and are of a width, height and spacing sufficient to permit the looping of the matrix band through the slots to form a plurality of loops for binding engagement with the teeth; and a mounting means for mounting the elongated member to a conventional matrix retainer in such a manner that the matrix band can be drawn into binding engagement with the teeth by the conventional matrix retainer, whereby when the matrix band is drawn into binding engagement with the teeth the elongated member and the matrix band substantially conform to the taper and the curvature of the teeth.

15. The matrix band guide of claim 14, wherein the mounting means is a detachable mounting means for detachably mounting the elongated member to the conventional matrix retainer.

16. The matrix band guide of claim 14, wherein there are five slots.

17. The matrix band guide of claim 14, wherein the slots are closed at both ends.

18. The matrix band guide of claim 14, wherein the elongated member is transparent.

19. A matrix retainer device for use in simultaneously applying a matrix band to a plurality of teeth comprised of:

a matrix band guide having a flexible elongated member having a plurality of slots, wherein the elongated member is of sufficient length and sufficient width to allow placement of the guide against the teeth and to guide the matrix band around the teeth, and wherein the slots extend a major portion of the width of the member and are of a width, height and spacing sufficient to permit the looping of the matrix band through the slots to form a plurality of loops for binding engagement with the teeth; and attached to the guide a means for drawing a matrix band into binding engagement with the teeth, whereby when the matrix band is drawn into binding engagement with the teeth the elongated member and the matrix band substantially conform to the taper and curvature of the teeth.

20. The matrix retainer device of claim 19, wherein there are five slots.

21. The matrix retainer device of claim 19, wherein there are four slots.

22. The matrix retainer device of claim 19, wherein there are three slots.

23. The matrix retainer device of claim 19, wherein there are two slots.

24. The matrix retainer device of claim 19, wherein the slots are closed at both ends.

25. The matrix retainer device of claim 19, wherein the elongated member is transparent.

26. A matrix retainer device for use in simultaneously applying a matrix band to a plurality of teeth comprised of:

a matrix band guide having a flexible elongated member having a plurality of slots, wherein the elongated member is of sufficient length and sufficient width to allow placement of the guide against the teeth and to guide the matrix band around the teeth, and is shaped to substantially conform to the alignment of the teeth, and wherein the slots extend a major portion of the width of the member and are of a width, height and spacing sufficient to permit the looping of the matrix band through the slots to form a plurality of loops for binding engagement with the teeth; and attached to the guide a means for drawing a matrix band into binding engagement with the teeth, whereby when the matrix band is drawn into binding engagement with the teeth the elongated member and the matrix band substantially conform to the taper and curvature of the teeth.

27. The matrix retainer device of claim 26, wherein there are five slots.

28. The matrix retainer device of claim 26, wherein the slots are closed at both ends.

29. The matrix retainer device of claim 26, wherein the elongated member is transparent.

* * * * *